United States Patent
Leone

(10) Patent No.: US 11,723,561 B2
(45) Date of Patent: Aug. 15, 2023

(54) SYSTEMS AND METHODS FOR HEMATOCRIT IMPEDANCE MEASUREMENT USING SWITCHED CAPACITOR ACCUMULATOR

(71) Applicant: Trividia Health, Inc., Fort Lauderdale, FL (US)

(72) Inventor: Steven V. Leone, Lake Worth, FL (US)

(73) Assignee: Trividia Health, Inc., Fort Lauderdale, FL (US)

(*) Notice: Subject to any disclaimer, the term of this patent is extended or adjusted under 35 U.S.C. 154(b) by 351 days.

(21) Appl. No.: 16/787,417

(22) Filed: Feb. 11, 2020

(65) Prior Publication Data

US 2020/0253514 A1 Aug. 13, 2020

Related U.S. Application Data

(60) Provisional application No. 62/803,732, filed on Feb. 11, 2019.

(51) Int. Cl.
*A61B 5/145* (2006.01)
*G01N 27/327* (2006.01)
(Continued)

(52) U.S. Cl.
CPC ...... *A61B 5/14532* (2013.01); *A61B 5/14535* (2013.01); *G01N 27/3274* (2013.01); *H01G 9/26* (2013.01)

(58) Field of Classification Search
CPC ............ A61B 5/14532; A61B 5/14535; A61B 5/1486; A61B 5/7225; G01N 27/3274; G01N 27/3273; H01G 9/26
See application file for complete search history.

(56) References Cited

U.S. PATENT DOCUMENTS 9,261,477 B2 * 2/2016 McColl .............. G01N 27/3274
2004/0079652 A1 * 4/2004 Vreeke ................... G01N 33/66
205/777.5
(Continued)

FOREIGN PATENT DOCUMENTS

WO 2018115135 A1 6/2018

OTHER PUBLICATIONS

N. Kordas, "The properties of integrated micro-electrodes for CMOS-compatible medical sensors", 1994, IEEE (Year: 1994).*

(Continued)

*Primary Examiner* — Christian Jang
*Assistant Examiner* — Clarissa Cuevas
(74) *Attorney, Agent, or Firm* — Greenberg Traurig, LLP; David J. Dykeman; Roman Fayerberg

(57) ABSTRACT

There is provided a system for measuring a property of a sample that comprises a test strip for collecting the sample; a diagnostic measuring device configured to receive the test strip and measure a concentration of an analyte in the sample received on the test strip; and the diagnostic measuring device further comprising a processor programmed to execute an analyte correction for correcting a measurement of the sample due to one or more interferents, comprising: calculating an interferent impedance measurement including a magnitude measurement and a phase measurement using a switched capacitor accumulator to measure a phase angle; and adjusting the measurement of the analyte in the sample using that the calculated interferent impedance measurement.

11 Claims, 12 Drawing Sheets

(51) Int. Cl.
*H01G 9/26* (2006.01)
*A61B 5/1486* (2006.01)
*A61B 5/00* (2006.01)

(56) References Cited

U.S. PATENT DOCUMENTS

| | | |
|---|---|---|
| 2009/0157344 A1* | 6/2009 | Burke ................ G01N 27/3274 |
| | | 702/106 |
| 2014/0251833 A1 | 9/2014 | Smith et al. |
| 2014/0353176 A1 | 12/2014 | Elder et al. |
| 2015/0001097 A1* | 1/2015 | Malecha ............ G01N 27/3274 |
| | | 205/777.5 |
| 2015/0073718 A1 | 3/2015 | Elder et al. |
| 2016/0299097 A1 | 10/2016 | Lloyd et al. |
| 2017/0185733 A1 | 6/2017 | Nogueira et al. |
| 2018/0321179 A1 | 11/2018 | Leone |

OTHER PUBLICATIONS

Shashank Kalvacharla, "Measurement of Fractional Impedance using Switch Capacitor Circuits", 2017 (Year: 2017).*
Arthur Pini, "Measure phase difference with an oscilloscope", 2018 (Year: 2018).*
PCT International Search Report in PCT International Application No. PCT/US2020/017649 dated May 4, 2020.

* cited by examiner

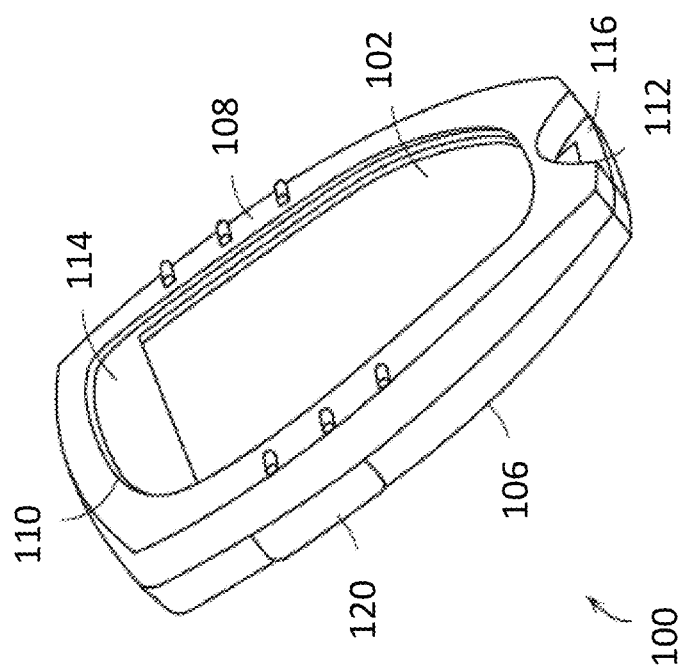

SYSTEMS AND METHODS FOR HEMATOCRIT IMPEDANCE MEASUREMENT USING SWITCHED CAPACITOR ACCUMULATOR

RELATED APPLICATIONS

This application claims the benefit of and priority to U.S. Provisional Application No. 62/803,732, filed Feb. 11, 2019, the entirety of which is hereby incorporated herein by reference.

FIELD

The present disclosure relates to systems and methods for hematocrit impedance measurement in connection with blood glucose and hemoglobin meters.

BACKGROUND

Many industries have a commercial need to monitor the concentration of particular constituents in a fluid. In the health care field, for example, individuals with diabetes have a need to monitor a particular constituent within their bodily fluids. A number of systems are available that allow people to test a body fluid, such as, blood, urine, or saliva, to conveniently monitor the level of a particular fluid constituent, such as, cholesterol, proteins, and glucose. Such systems typically include a test strip where the user applies a fluid sample and a meter that "reads" the test strip to determine the level of the tested constituent in the fluid sample. A Blood Glucose Monitor (BGM) is an example of such a device. A hemoglobin meter (HbM) is another.

Conventionally, a BGM is a portable handheld device used to measure blood glucose levels for users with Type I or Type II diabetes. Typically, the user purchases small strips (approximately 20-30 mm×5-9 mm) that interface with the BGM or HbM. The user draws a tiny amount of blood (a few microliters) from a finger or other area using a lancer, applies a blood droplet sample onto the exposed end of the strip, and then inserts the connector end of the strip into the BGM connector port. A chemical reaction occurs between the blood sample and the chemistry on the strip, which is measured by the BGM to determine the blood glucose level in units of mg/dL or mmol/L, or Kg/L depending on regional preferences. Units for hemoglobin (Hb) are in g/dL Two resources that are constrained in handheld blood glucose meter (BGM) and hemoglobin meter (HbM) designs are energy and processing power. To keep the cost and size down, portable BGMs are typically powered by a small single CR2032 type coin cell Lithium battery or similar. The peak source current of this type of battery is very low and the total current capacity is also very low, from tens to a few hundred milli-Amp-hours (mAh). Yet, this small battery is expected to last the life of the meter, or at least require extremely infrequent battery changes. A dead battery would present an opportunity for the customer to purchase a competitor's brand meter and thereby purchase the competitors strips going forward.

SUMMARY

The present disclosure relates to systems and methods for hematocrit impedance measurement in connection with blood glucose and hemoglobin meters.

In some aspects, the present disclosure provides a system for measuring a property of a sample that comprises a test strip for collecting the sample; a diagnostic measuring device configured to receive the test strip and measure a concentration of an analyte in the sample received on the test strip; and the diagnostic measuring device further comprising a processor programmed to execute an analyte correction for correcting a measurement of the sample due to one or more interferents, comprising: calculating an interferent impedance measurement including a magnitude measurement and a phase measurement using a switched capacitor accumulator to measure a phase angle; and adjusting the measurement of the analyte in the sample using that the calculated interferent impedance measurement.

In some aspects, the present disclosure provides a system for measuring a property of a sample, comprising a diagnostic measuring device configured to measure a concentration of an analyte in a sample; and the diagnostic measuring device further comprising a processor programmed to execute an analyte correction for correcting a measurement of the sample due to one or more interferents, comprising: calculating an interferent impedance measurement including a magnitude measurement and a phase measurement using a switched capacitor accumulator to measure a phase angle; and adjusting the measurement of the analyte in the sample using that the calculated interferent impedance measurement.

In some aspects, the present disclosure provides a method of measuring a property of a sample comprising: measuring an analyte in a sample; performing an analyte correction of the measured analyte due to one or more interferents, comprising: calculating an interferent impedance measurement including a magnitude measurement and a phase measurement using a switched capacitor accumulator to measure a phase angle; and adjusting the measurement of the analyte in the sample using that the calculated interferent impedance measurement.

In some embodiments, the at least one interferent is hematocrit. In some embodiments, the test strip comprises: a conductive pattern including at least one electrode at the proximal region of the test strip, electrical strip contacts disposed at a conductive region at the distal region of the test strip, and conductive traces electrically connecting the electrodes to at least some of the electrical strip contacts; a reagent layer contacting at least a portion of at least one electrode; and a chamber at the proximal region of the test strip for receiving the sample. In some embodiments, measuring the phase angle comprises accumulating time differences that represent phase over a sample window to generate a signal large enough to be measured to calculate the phase measurement. In some embodiments, the switched capacitor accumulator can measure the phase measurement at high frequencies. In some embodiments, the frequency can be up to 500 kHz.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 2A and 2B illustrate a meter according to some embodiments of the present disclosure;

Figure 1A:
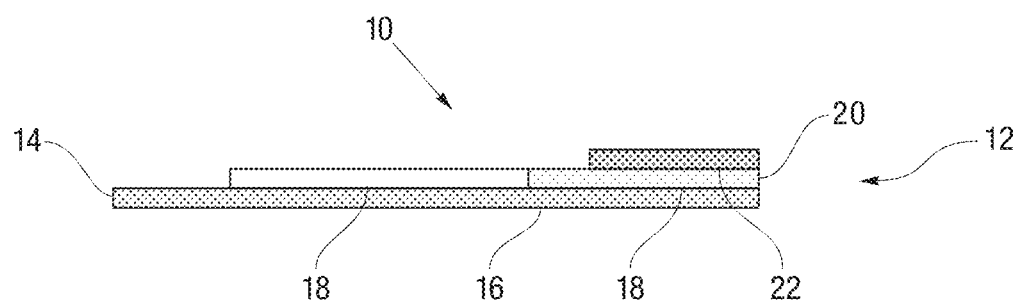
FIG. 1A is a general cross-sectional view of a test strip according to some embodiments of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In order to determine a measurement of an analyte, such as blood glucose, in a sample, such as blood, using a device, such as a blood glucose meter, certain interferents can be accounted for to increase the accuracy of the measurement. For example, one such interferent is the hematocrit (HCT) concentration in the blood. In some embodiments, a method of measuring the HCT for a blood glucose meter using the current response to a step voltage excitation input, including peak current, and decay rate can be mapped to various HCT levels.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments Specific details are given in the following description to provide a thorough understanding of the embodiments. However, it will be understood by one of ordinary skill in the art that the embodiments may be practiced without these specific details. For example, systems, processes, and other elements in the presently disclosed embodiments may be shown as components in block diagram form in order not to obscure the embodiments in unnecessary detail. In other instances, well-known processes, structures, and techniques may be shown without unnecessary detail to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Subject matter will now be described more fully with reference to the accompanying drawings, which form a part hereof, and which show, by way of illustration, specific example aspects and embodiments of the present disclosure. Subject matter may, however, be embodied in a variety of different forms and, therefore, covered or claimed subject matter is intended to be construed as not being limited to any example embodiments set forth herein; example embodiments are provided merely to be illustrative. The following detailed description is, therefore, not intended to be taken in a limiting sense.

A Blood Glucose Meter (BGM) is a portable, handheld device used to measure blood glucose levels for users with Type I or Type II diabetes. A Hemoglobin (HbG) meter measure blood hematocrit to compute Hemoglobin.

Typically, the user purchases tiny strips that interface with the BGM. The user draws a tiny amount of blood (a few microliters or less) from a finger or other area using a lancer. They then insert the strip into the BGM connector port. Now they apply the blood droplet onto the exposed end of the strip which has an open port for the blood. A chemical reaction occurs between the blood sample and the chemistry on the strip, which is measured by the BGM to determine the blood glucose level in units of mg/dL or mmol/L, depending on regional preferences and hematocrit as a percentage. Alternately, continuous blood glucose meters measure blood that is continuously provided via a patch. Hemoglobin is measured in g/dL.

The BGM measures blood glucose by analyzing the electrical response to an excitation signal. However, this response is dependent on the hematocrit (HCT) concentration in the blood. The accuracy of the glucose measurement is therefore dependent on the accuracy of the HCT concentration to compensate the measurement for this interferent.

The present disclosure provides systems and methods for hematocrit measurement. In particular, the present disclosure provides systems and methods for obtaining a hematocrit impedance measurement for a blood glucose meter. In some embodiments, a low cost low power microcontroller can be used to measure complex impedance. No high sampling rates are needed for high frequency signals for magnitude and phase measurements. In some embodiments, a phase measurement using the switched capacitor accumulator method can take fast, narrow time pulse measurements and accumulate them over a sample window so the phase can be measured accurately without high precision instrumentation. The present disclosure provides a switched capacitor accumulator method to measure narrow pulse phase at high frequencies (up to 500 kHz). In some embodiments, peak detector circuits can be used to allow easy measurement of impedance magnitude with low cost, low power microcontroller suitable for handheld devices.

A meter for measuring blood glucose or another analyst can include a portable, handheld device used to measure blood glucose levels for users with Type I or Type II diabetes. Typically, the user purchases test strips that interface with the meter. The user draws a tiny amount of blood (a few microliters or less) from a finger or other area using a lancer and a blood droplet is applied onto the exposed end of the strip which has an open port for the blood. The strip is inserted into the meter connector port and a chemical reaction occurs between the blood sample and the chemistry on the strip, which is measured by the meter to determine the blood glucose level in units of mg/dL or mmol/L, depending on regional preferences.

FIG. 1A illustrates a general cross-sectional view of an example embodiment of a test strip 10. In particular, FIG. 1A depicts a test strip 10 that includes a proximal end 12, a distal end 14, and is formed with a base layer 16 extending along the entire length of test strip 10. The base layer 16 is preferably composed of an electrically insulating material and has a thickness sufficient to provide structural support to test strip 10. For purposes of this disclosure, "distal" refers to the portion of a test strip further from the fluid source (e.g., closer to the meter) during normal use, and "proximal" refers to the portion closer to the fluid source (e.g., a fingertip with a drop of blood for a glucose test strip) during normal use. The base layer 16 may be composed of an electrically insulating material and has a thickness sufficient to provide structural support to test strip 10.

As seen in FIG. 1A, the proximal end 12 of test strip 10 includes a sample receiving location, such as a sample chamber 20 configured to receive a patient's fluid sample, as described above. The sample chamber 20 may be formed in part through a slot in a dielectric insulating layer 18 formed between a cover 22 and the underlying measuring electrodes formed on the base layer 16. Accordingly, the sample chamber 20 may include a first opening, e.g., a sample receiving location, in the proximal end of the test strip and a second opening for venting the sample chamber 20. The sample chamber 20 may be dimensioned to be able to draw the blood sample in through the first opening, and to hold the blood sample in the sample chamber 20, by capillary action. The test strip 10 can include a tapered section that is narrowest at the proximal end 12, or can include other indicia to make it easier for the user to locate the first opening and apply the blood sample.

Figure 1B:
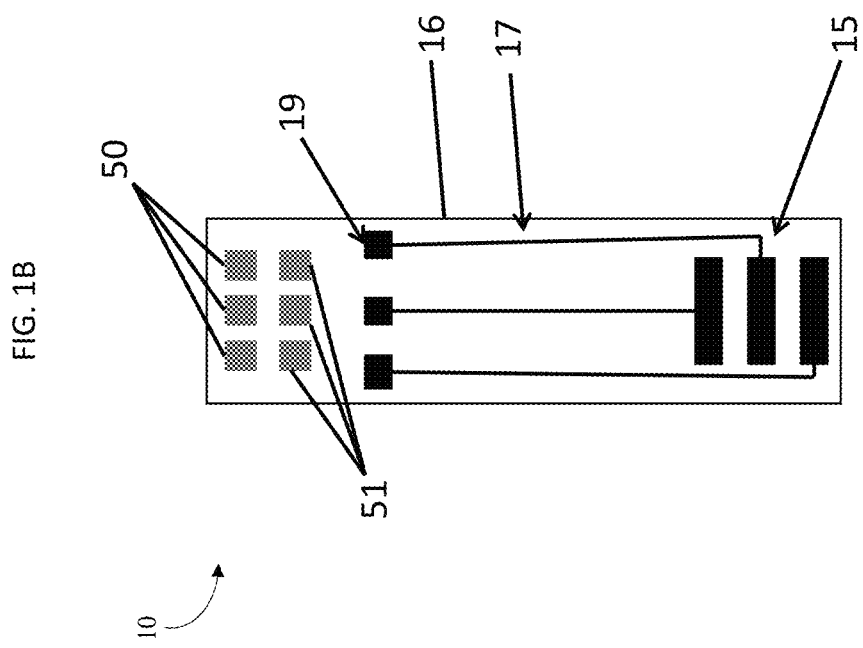
FIG. 1B is a top view of a conductive pattern on a substrate of a test strip according to some embodiments of the present disclosure.

In reference to FIG. 1B, in accordance with an example embodiment of the present disclosure, the strip 10 can include a conductive pattern disposed on base layer 16 of the strip 10. In some embodiments, the conductive pattern may be formed by laser ablating the electrically insulating material of the base layer 16 to expose the electrically conductive material underneath. Other methods may also be used, such as inserted conductors with physical attachment to control circuit. Other methods may also be used to dispose the conductive pattern on the base layer. The conductive pattern may include a plurality of electrodes 15 disposed on base layer 16 near proximal end 12, a plurality of electrical strip contacts 19 disposed on base layer 16 near distal end 14, and a plurality of conductive traces 17 electrically connecting the electrodes 15 to the plurality of electrical strip contacts 19.

In some embodiments, a reagent layer may be disposed on the base layer 16 of the strip 10 in contact with at least a working electrode of the conductive pattern. The reagent layer may include an enzyme, such as glucose oxidase, and a mediator, such as potassium ferricyanide or ruthenium hexamine. Reagent layer 90 may also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485). With these chemical constituents, the reagent layer reacts with glucose in the blood sample in the following way. The glucose oxidase initiates a reaction that oxidizes the glucose to gluconic acid and reduces the ferricyanide to ferrocyanide. When an appropriate voltage is applied to working electrode, relative to counter electrode, the ferrocyanide is oxidized to ferricyanide, thereby generating a current that is related to the glucose concentration in the blood sample. As would be appreciated by one skilled in the art, any combination of strips 10 known in the art can be utilized without departing from the scope of the present disclosure.

Figure 2A:
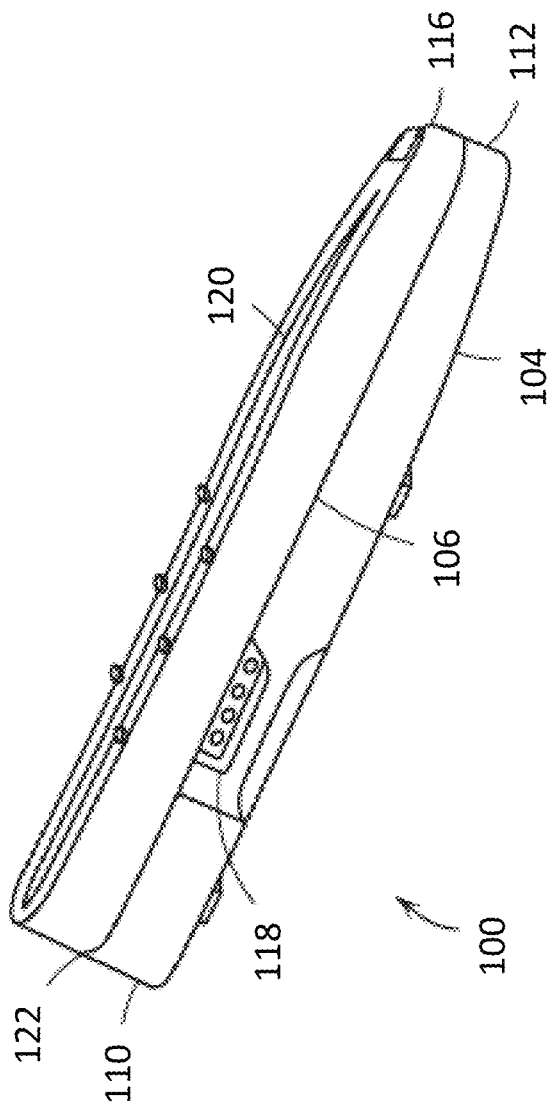

FIG. 2A and FIG. 2B illustrate an exemplary illustration of a meter 100 used to measure the glucose level in a blood sample. The meter 100 includes a housing having a test port for receiving the test strip, and a processor or microprocessor programmed to perform methods and algorithms to determine glucose concentration in a test sample or control solution as disclosed in the present disclosure. In some embodiments, the meter 100 has a size and shape to allow it to be conveniently held in a user's hand while the user is performing the glucose measurement. The meter 100 may include a front side 102, a back side 104, a left side 106, a right side 108, a top side 110, and a bottom side 112. The front side 102 may include a display 114, such as a liquid crystal display (LCD). A bottom side 112 may include a strip connector 116 into which test strip can be inserted to conduct a measurement. The meter 100 may also include a storage device for storing test algorithms or test data. The left side 106 of the meter 100 may include a data connector 118 into which a removable data storage device 120 may be inserted, as necessary. The top side 110 may include one or more user controls 122, such as buttons, with which the user may control meter 100, and the right side 108 may include a serial connector (not shown).

In some embodiments, the blood glucose meter comprises a decoder for decoding a predetermined electrical property, e.g. resistance, from the test strips as information. The decoder operates with, or is a part of, the microprocessor.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample to determine the particular glucose concentration. In one example, glucose oxidase is used in the reagent layer. The recitation of glucose oxidase is intended as an example only and other materials can be used without departing from the scope of the present disclosure. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user.

A correction based on a measured HCT value can be applied to glucose level determined by the meter. In some embodiments, the HCT measurement sequence begins after a drop of blood or control is detected when the drop completes the circuit between the HCT measurement anode and cathode. In some embodiment, the HCT is analyzed based on an electrical measurement between two electrodes on the test strip separate from the electrodes used to measure glucose, or the electrodes can be shared for both measurements. After the drop is detected and either before, during, or after glucose measurement in the case of a glucose meter, an excitation voltage signal is applied to the HCT electrodes. The salt content of blood creates an electronic signature, in which the magnitude and phase response can be mapped to the HCT of the blood. The impedance of the electrical signature is affected by temperature, so the true HCT reading is corrected for temperature for the temperature difference from 24° C. (dT).

In some embodiments, the glucose measurement sequence is initiated only when the meter detects a full sample chamber. The glucose in the test sample is oxidized by the enzyme glucose dehydrogenase-FAD, producing gluconolactone and the reduced form of an electron mediator. The reduced mediator is then oxidized at the surface of the glucose measurement anode to produce an electrical signal (current in nanoamp units) that is detected by the meter. The electrical signal (current, in nanoamps) produced by oxidation of the reduced mediator at the surface of the glucose measurement anode is proportional to the amount of glucose in the test sample. The HCT value (which can be temperature corrected) is then used to determine the temperature corrected glucose value.

The meter can measure blood glucose by analysing the electrical response to an excitation signal. However, this response is dependent on the HCT concentration in the blood. The accuracy of the glucose measurement is therefore dependent on the accuracy of the HCT concentration to compensate the measurement for this interferent. For a given blood glucose sample, the peak response current to a voltage excitation used to measure blood glucose on the blood sample can be inversely proportional to the HCT concentration in the blood. Knowing the HCT impedance provides the data to map the HCT concentration to the peak current through empirical methods. This known HCT concentration (% HCT) can then be used to adjust blood glucose measurement. Hemoglobin concentration is converted directly from percent HCT.

Various systems and methods can be used for measuring the HCT concentration from step response to impedance measurement. In some embodiments, a method of measuring the HCT for a blood glucose meter includes using multiple setpoints of relatively high frequency (10 kHz-500 kHz) magnitude and phase measurements to measure the HCT impedance. In some embodiments, the phase measurement is done using narrow time pulse measurements that can be accumulated over a sample window.

In some embodiments, a method of measuring the HCT for a blood glucose meter can mix analog and digital circuitry to measure the HCT complex impedance (HCT impedance magnitude and phase).

One limitation of many microcontrollers suitable for handheld meters is that they have limited sampling rates making accurate magnitude and timing resolution for phase difficult. In some embodiments, both magnitude and phase signals are offloaded to separate analog circuitry for processing and converted to a simple DC output measurement suitable for most microcontrollers.

Figure 5:
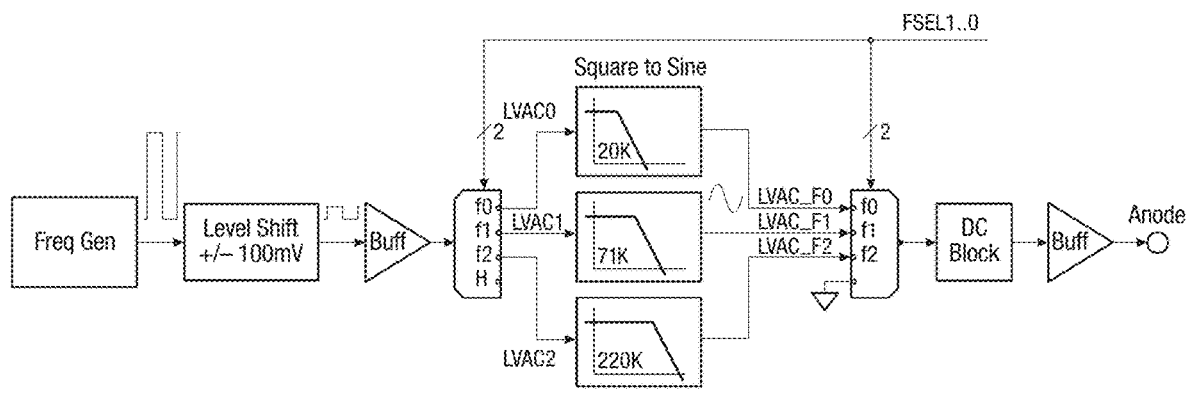
FIG. 5 is an exemplary excitation signal chain circuit diagram.

Additionally, in some embodiments, measurements can be taken at a plurality of frequencies. In some embodiments, frequencies in the range of 10 kHz to 500 kHz can be used. For example, measurements can be taken at up to three different frequencies (e.g. 20 kHz, 71 kHz, 200 kHz). A unique method can be provided for generating up to 3 frequencies, but more can be easily extended. To generate the frequencies, as described in FIG. 5, a squarewave can be generated by a microcontroller at the frequency of interest and is then multiplexed to the matching analog low pass filter circuit to generate a pure sine wave excitation at this frequency. The microcontroller can generate these digital frequencies and the analog circuitry can have a multiplexer input/output for each unique frequency desired as well as a low pass filter for each unique frequency desired. For example, FIG. 5 shows three unique frequencies with three multiplexer outputs and three low pass filters. Furthermore, in some embodiments DC bias is not desirable when exciting the blood sample, and too high an excitation amplitude can damage the sample. Therefore, the maximum signal amplitude can be very low (<100 mV), be in the form of a pure sine wave, and have 0 DC bias.

Magnitude

The magnitude of the impedance is a measure of $V(\omega)/I(\omega)$. This presents a challenge to most microcontrollers as the frequency of excitation can become high, for example, a range of 10 kHz-500 Khz. The solution lies in accurately detecting the peak of $V(\omega)$ and the peak of $I(\omega)$ and computing the magnitude as $$|Z(\omega)|=Vpk(\omega)/Ipk(\omega)$$

Figure 3:
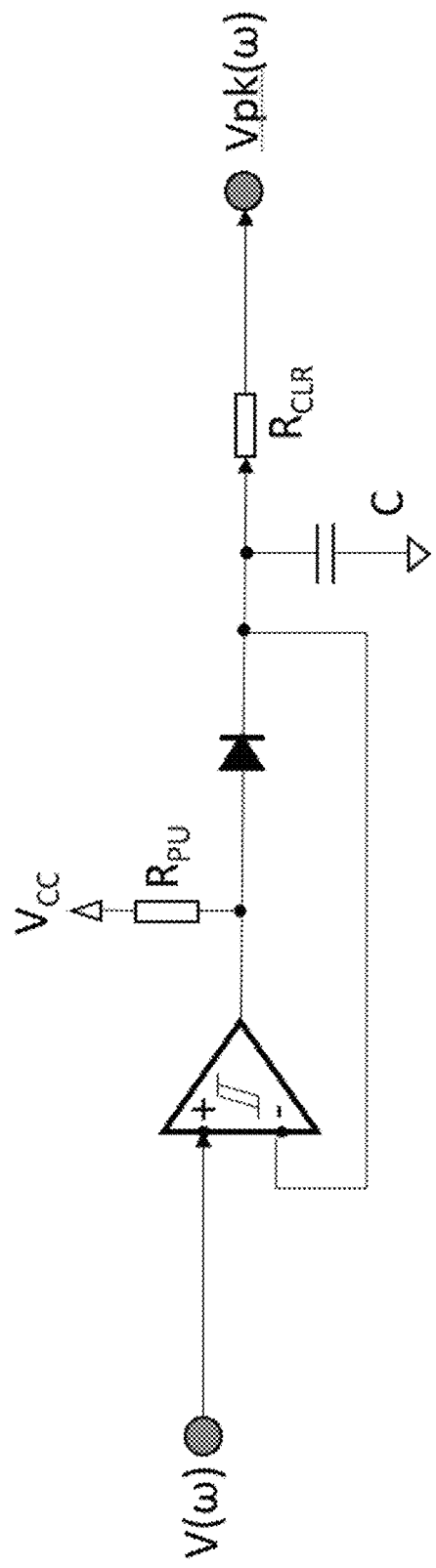
FIG. 3 illustrates an exemplary embodiment of a voltage peak detector.

FIG. 3 illustrates an exemplary embodiment of a $V(\omega)$ peak detector using a comparator for high frequencies measurement of peak voltage. When an AC voltage is applied to the non-inverting input of the comparator (+input), if the voltage on the capacitor is less than the peak input voltage, then the comparator output will go "open collector" and charge the capacitor through $R_{PU}$, until capacitor C is charged to the peak voltage at a DC level. Each AC cycle the capacitor discharges a little but is refreshed by the comparator each cycle to keep a stable DC voltage on the capacitor which is read by the microcontroller on and analog to digital (ADC) channel. Once the measurement is complete, the microcontroller will switch the ADC input function to GPIO output LO to discharge the capacitor to start a fresh measurement without residual voltage from the last measurement. The output $Vpk(\omega)$ is the demodulated DC output input to an ADC through $R_{CLR}$, which is chosen to be a small resistance, such as $100\Omega$, as needed for an accurate measurement by an ADC. This input to the ADC can then be switched to a digital output, active LO to clear the output for the next measurement.

Figure 4:
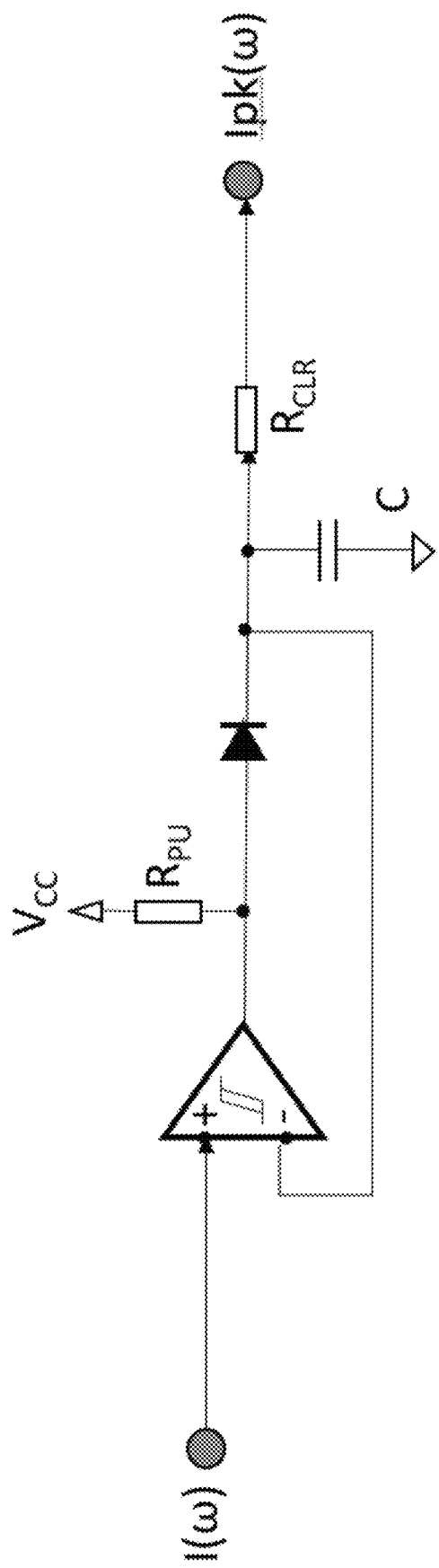
FIG. 4 illustrates an exemplary embodiment of a current peak detector.

At high frequencies, for example up to 500 kHz, most peak detection using op amps will not accurately measure the peak. In some embodiments, a comparator is used to accurately measure peaks at high frequencies. FIG. 4 illustrates an exemplary embodiment of a $I(\omega)$ peak detector using a comparator for high frequencies measurement of peak current. $I(\omega)$ is an AC sinusoidal voltage signal that is proportional to current. The circuit in FIG. 4 functions the same as the circuit in FIG. 3 except the voltage input/output is a scaled representation of the current.

Various comparators can be used to measure peak voltage and/or peak current. In some embodiments, rail to rail input and output comparators can be used. Furthermore, the power supplies can be bipolar (±V) to support the sinusoidal AC input signal which swings between negative maximums, through zero (zero bias), to positive maximums. A pullup resistor of (1kΩ-4.99kΩ) can provide a quick charge of capacitor C each sinusoidal cycle. When the measurement is done, the signal can be cleared by switching the ADC input of Ipk(ω) to a GPIO output and clear the peak voltage Vpk(ω) before the next measurement by driving the output LO. $R_{CLR}$ should be in the range of a few hundred ohms to discharge the capacitor quickly.

Excitation Signal Chain

As shown in FIG. 5, the microcontroller generates a square wave digital excitation at the desired frequency (up to 500 kHz). This is easily accomplished on most low cost low power microcontrollers capable of operating at bus speeds of 8 MHz or greater. This signal is a digital 0-3V level and can be processed into a pure sine wave at <100 mV amplitude and 0 DC bias. For example, an acceptable output signal would be ±90 mV sine wave, centered around ground (0V). This level shifting results in a low level square wave signal going positive and negative centered around zero volts. This low level signal is buffered to provide impedance matching before being sent to the multiplexer where one of three low pass filters will convert the low level square wave signal into a low level sinusoidal signal by filtering out all frequencies for the square wave except the fundamental. The output of the selected low pass filter is then multiplexed to the next stage where any resultant DC error offset is removed with a DC block circuit, usually just a passive RC high pass filter. Finally, the low level AC signal is buffered for impedance matching and output to the anode electrode. FIG. 5 illustrates an exemplary V(ω) excitation signal chain block diagram.

Figure 6:
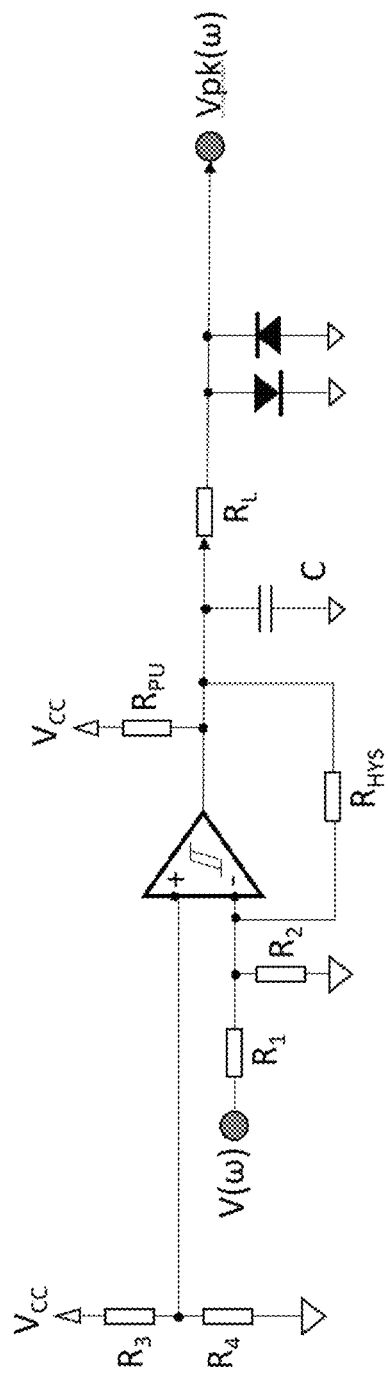
FIG. 6 is an exemplary circuit for level shifting a digital signal.

Therefore, the digital excitation is level shifted to ±(<100 mV) and buffered. This level shifting can be accomplished using a combination of comparator and Schottky diodes, as shown in FIG. 6. FIG. 6 Illustrates a circuit for level shifting a digital signal to ±($V_D$) using one schottky diode drop of ~400 mV. V(ω) is scaled down by R1/R2 and is compared to the DC reference voltage generated by R3/R4 voltage divider from $V_{CC}$ supply voltage. This generates an AC output voltage that swings from +$V_{CC}$ to -$V_{EE}$ supplying the comparator (example ±2.75V). RHYS provides hysteresis so there is no gitter on transitions around the reference voltage switchover point. The comparator output swings from open collector to negative supply, as V(ω) swings from positive to negative each AC cycle. On the open collector cycle, D1 is forward biased and conducts resulting in an output voltage one diode drop +$V_D$. On the negative cycle, the output of the comparator is -$V_{EE}$ (example -2.75V) and D2 conducts resulting in an output voltage of one diode drop -$V_D$, typically ±400 mV AC signal is generated by this circuit. $R_{PU}$ is needed because the comparator is typically an open collector type which uses the energy of $V_{CC}$ to provide a HI level output $R_L$ can limit the current through $D_1/D_2$.

The next step is to select the proper low pass analog filter to pass the signal through. Once this step is taken, the signal will be a pure sine wave (<±100 mV) amplitude, as the filtering process reduces the signal amplitude as higher frequency harmonics are attenuated. A frequency is chosen by the microcontroller using two digital control lines FSEL1 and FSEL0.

The low pass filters can be any combination of active or passive low pass filters to achieve a $4^{th}$ order attenuation at the chosen frequency. In some embodiments, low pass filters that can be used include but are not limited to a Sallen-key filter and a Bessel filter.

Finally, the sine wave chosen is sent to a DC block circuit before being buffered to excite the anode electrode.

Figure 7:
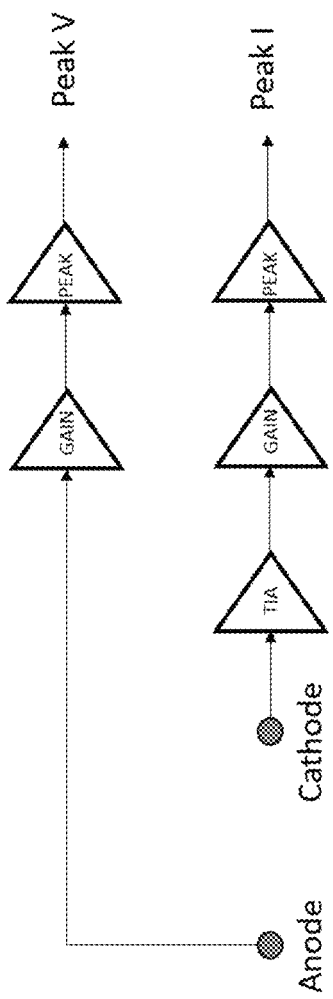
FIG. 7 is an exemplary circuit for magnitude measurement.

The cathode current is measured with a transimpedance amplifier (TIA) which generates a current proportional to voltage, in this case at the frequency of excitation. Both the excitation signal and current response signal are amplified through gain stages and the peaks extracted. These peaks are DC measurements read by the microcontroller's analog to digital converter (ADC) channels (FIG. 7). FIG. 7 shows two electrodes (anode and cathode). The anode, excited by voltage excitation V(w) goes to a gain stage with peak detected to be measured by the microcontroller ADC. The cathode, where current flow from the blood sample into the TIA to generate an AC voltage proportional to the AC current, then goes to a gain stage with peak detected to be measured by the microcontroller ADC.

The impedance magnitude is calculated as the ratio:

$$|Z|=\text{Peak } V/\text{Peak } I$$

Phase Measurement

The phase measurement is an important part of the complex impedance. Magnitude by itself does not provide for the reactance component Xc.

The problem with the phase measurement is that at high frequencies the time difference that the phase represents is too small to measure with microcontrollers suitable for handheld devices. For example, 1° phase at 220 kHz is equal to only 12.6 ns, which would be too small to accurately measure with timer capture channels on low cost low power microcontrollers suitable for handheld devices.

In some embodiments, measuring the phase angle is accomplished by accumulating these small time differences over a sample window to provide a larger signal to measure representing the phase.

Switched Capacitor Accumulator

Figure 8:
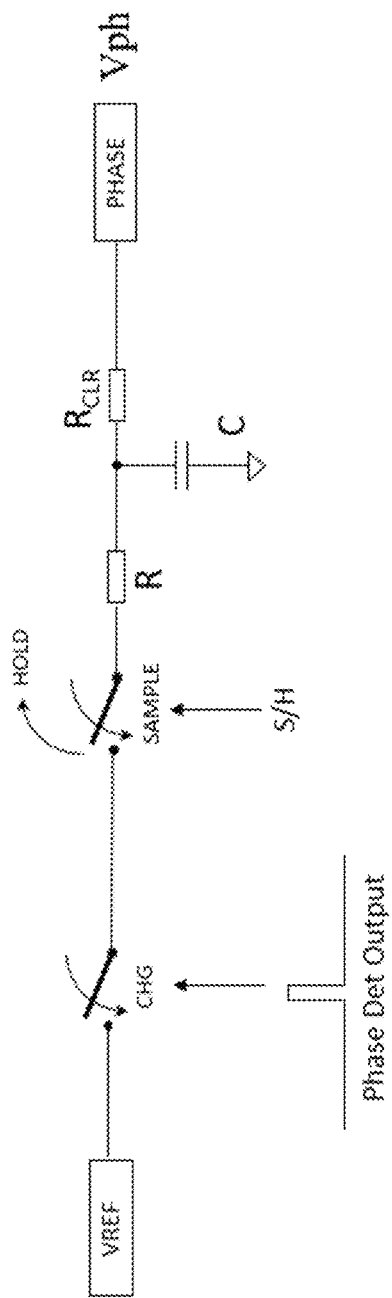
FIG. 8 is an exemplary switch capacitor accumulator.

An exemplary embodiment of a switched capacitor accumulator for narrow pulse phase measurement is shown in FIG. 8. Narrow phase pulses can be generated by a phase detector. This can be any well known technique such as XOR, flip flop, etc. These narrow pulses enable a SPST analog switch which connects a reference voltage to the charge circuit. A second SPST analog switch in series with the first acts as a sample and hold. During a known sample window, the reference voltage will charge the RC circuit to ramp up a voltage proportional to the phase angle.

Once the sample window is done, the value is held by the sample and hold (S/H switch open) so the microcontroller can read the DC voltage. Finally, after the signal is read, the voltage on the capacitor is discharged by changing the ADC input phase to a GPIO output LO to clear the signal for the next measurement.

Figure 9:
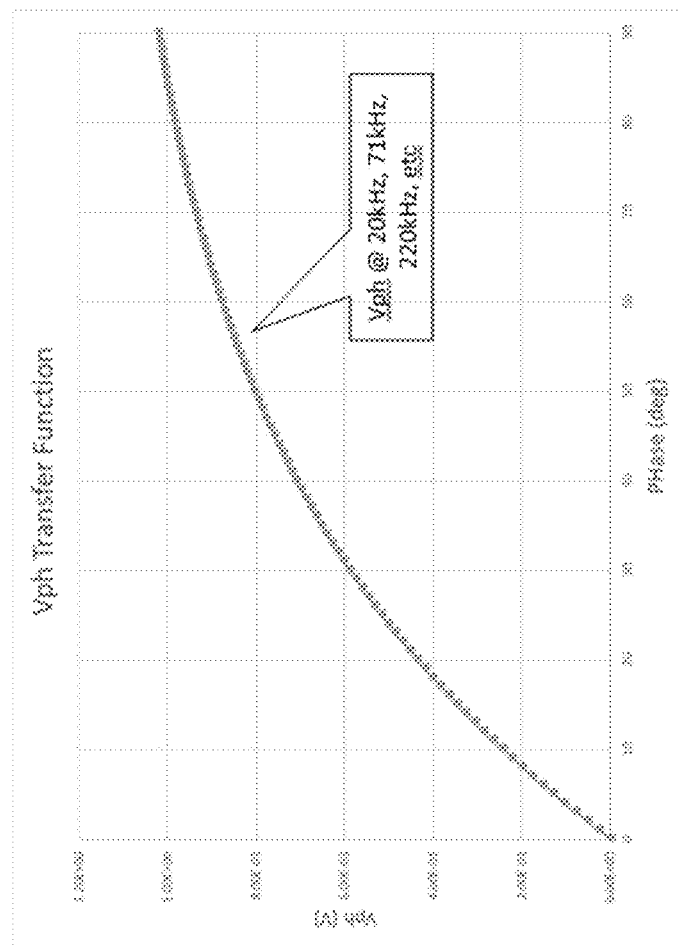
FIG. 9 is an exemplary graph showing phase as a function of terminal voltage from the switched capacitor accumulator circuit.

An exemplary graph depicting a transfer function of the switch capacitor accumulator is shown in FIG. 9. In an exemplary embodiment, resistance R=4.99 kΩ, and capacitance C=0.47 uF.

The transfer function is an RC charge over a sample window. A derivation shows that the phase is proportional to Vph from this circuit in the following nonlinear equation:

$$\phi = \frac{-RC\ln\left(1-\frac{V_{pk}}{V_R}\right)360°}{2T_w}$$

In some embodiments, the transfer function is independent of frequency. The phase only depends on the value of the resistance, capacitance, reference voltage (typically 1 to 1.5V) and the sample window $T_W$ and the value of Vph. Of these, only Vph is a variable, all others are known constants.

For example, for a sample window of 10 ms, the transfer function is dependent only on Vph as the other parameters are all constants.

$$\phi = -RC\ln\left(1-\frac{V_{pk}}{V_R}\right)18,000°$$

Different values of resistance and capacitance can be chosen depending on the range of phase of interest. For example, a larger time constant (RC), where R=4.99 kΩ and C=0.47 uF gives a larger range of phase (0°-90°) whereas a smaller time constant where R=2.2 kΩ and C=0.47 uF better for phases (0°-30°).

Once the phase is known, then together with the impedance magnitude, the reactance Xc can be calculated as:

$Xc = |Z|*\sin(\emptyset)$

Laboratory measurements map Xc to percent HCT concentrations. Known glucose concentrations are measured with different HCT percentages to map the interference. These adjustments are implemented into the glucose algorithms to compensate for the HCT interference. For example, at the same glucose levels, the impedance is higher at higher HCT. This can be compensated.

In some embodiments, the systems of the present disclosure may be used to measure glucose concentration in blood, among other measurements, as discussed above. Once the meter has performed an initial check routine, the meter can apply a drop-detect voltage between working and counter electrodes and detect a fluid sample, for example, a blood sample, by detecting a current flow between the working and counter electrodes (i.e., a current flow through the blood sample as it bridges the working and counter electrodes). For example, in some embodiments, the meter may measure an amount of components in blood which may impact the glucose measurement, such as, for example, a level of hematocrit or of an interferent. The meter can later use such information to adjust the glucose concentration to account for the hematocrit level and the presence of the interferents in blood, among other things. These measurements can also be corrected based on the temperature. The meter can then adjust the glucose level, as necessary, based on the measurements of the temperature, hematocrit and the presence of interferents. Non-limiting examples of algorithms for glucose level correction are presented in FIG. 10. Errors can be displayed if encountered.

Figure 10:
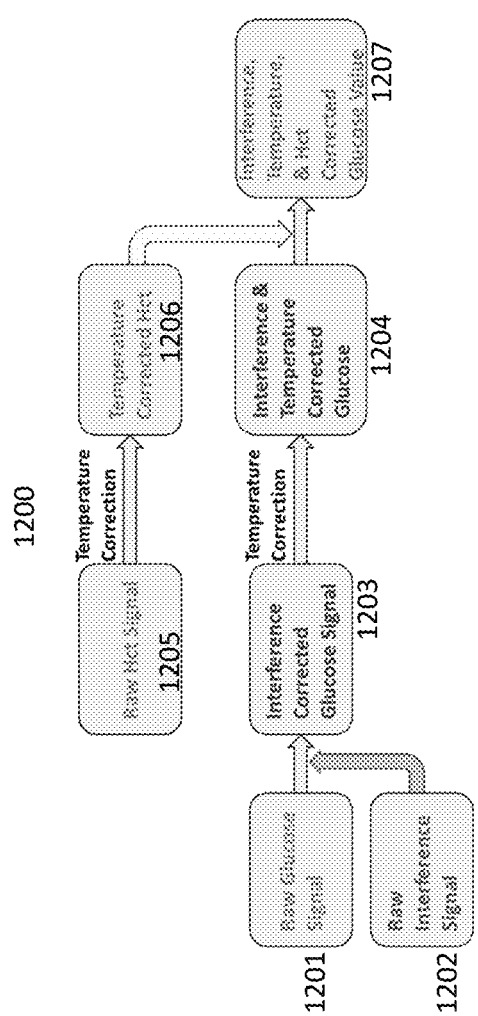
FIG. 10 is an exemplary flow chart showing an algorithm for correcting glucose measurements.

FIG. 10 is an embodiment flow chart for correcting the analyte value 1200, wherein the analyte specific current is modified based on temperature and hematocrit and interference currents to then generate a corrected analyte value. For example, equations may be IC=IA−S×II, where IC is the corrected current, IA is the current measured from the analyte anode, II is the current measured from the interference anode, and S is an empirically derived scaling factor. The present calculation may eliminate the need to make complicated calculation and/or voltage application schemes. The present calculation uses a mathematically modified (scaled) subtraction of the interference current from the current from the analyte specific anode. The interference current may be multiplied by an empirically determined constant that is dependent only on the relative areas of the two electrodes, not on the relative effects of hematocrit and temperature variations on the two currents. This is because the two reagents (analyte and interference) are formulated to respond the same way to hematocrit and temperature variations. Thus, referring to FIG. 10, the raw glucose signal 1201 would be corrected with the raw interference signal 1202 to obtain an interference corrected glucose signal 1203, where a temperature correction is incorporated to obtain an interference and temperature corrected glucose value 1204. The raw HCT signal 1205 is corrected to obtain a temperature corrected HCT 1206. The interference & temperature corrected glucose value 1204 may then be incorporated with the temperature corrected HCT 1206 to obtain an interference, temperature & HCT corrected glucose value 1207.

It is also possible to first make temperature and hematocrit adjustments to the interference current and then subtract it from the raw analyte current and then subject that corrected current to another temperature and hematocrit adjustment. In some embodiments, it may be possible to correct the analyte and interference currents separately for temperature and hematocrit, and then convert each separately to an uncorrected glucose value and to a glucose equivalent value, respectively. Then the glucose equivalent value can be subtracted from the uncorrected glucose value to obtain a corrected glucose value.

In some embodiments, it is possible to use the present calculation to also first convert the interference current to analyte equivalents and then subtract it from the amount of analyte of interference and subtract that number. That is, the correction can occur before or after mathematically processing the current. For example, by having the interference anode larger for improved signal to noise ratio due to the currents being so small, at least one aspect includes using a scaling factor and anodes of different surface area.

It should be noted that while the operation of the system of the present disclosure has been described primarily in connection with determining hematocrit concentration in blood to ultimately compute glucose concentration in blood, the systems of the present disclosure may be configured to measure other analytes in blood as well as in other fluids, as discussed above.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the disclosure. It is intended that the present disclosure be limited only to the extent required by the appended claims and the applicable rules of law.

It is also to be understood that the following claims are to cover all generic and specific features of the disclosure described herein, and all statements of the scope of the disclosure which, as a matter of language, might be said to fall therebetween.

What is claimed is:

1. A system for measuring a property of a sample, comprising:
   a test strip for collecting the sample;
   a diagnostic measuring device configured to receive the test strip and measure a concentration of an analyte in the sample received on the test strip; and
   the diagnostic measuring device further comprising a processor programmed to execute an analyte correction for correcting a measurement of the sample due to one or more interferents, comprising:
      calculating an interferent impedance measurement including a magnitude measurement and a phase measurement using a switched capacitor accumulator to measure a phase angle; and
      adjusting the measurement of the analyte in the sample using the calculated interferent impedance measurement
   wherein measuring the phase angle comprises measuring time differences using the switch capacitor accumulator within a sample window of multiple setpoints of frequency in the range of 10 kHz to 500 kHz and accumulating the time differences that represent phase over the sample window to generate a signal large enough to be measured to calculate the phase measurement.

2. The system of claim 1, wherein the analyte is glucose and the at least one interferent is hematocrit.

3. The system of claim 1, wherein the test strip comprises:
   a conductive pattern including at least one electrode at the proximal region of the test strip, electrical strip contacts disposed at a conductive region at the distal region of the test strip, and conductive traces electrically connecting the electrodes to at least some of the electrical strip contacts;
   a reagent layer contacting at least a portion of at least one electrode; and
   a chamber at the proximal region of the test strip for receiving the sample.

4. The system of claim 1, wherein the switched capacitor accumulator can measure the phase measurement at high frequencies.

5. A system for measuring a property of a sample, comprising:
   a diagnostic measuring device configured to measure a concentration of an analyte in a sample; and
   the diagnostic measuring device further comprising a processor programmed to execute an analyte correction for correcting a measurement of the sample due to one or more interferents, comprising:
      calculating an interferent impedance measurement including a magnitude measurement and a phase measurement using a switched capacitor accumulator to measure a phase angle; and
      adjusting the measurement of the analyte in the sample using the calculated interferent impedance measurement
   wherein measuring the phase angle comprises measuring time differences using the switch capacitor accumulator within a sample window of multiple setpoints of frequency in the range of 10 kHz to 500 kHz and accumulating the time differences that represent phase over a sample window to generate a signal large enough to be measured to calculate the phase measurement.

6. The system of claim 5, wherein the analyte is glucose and the at least one interferent is hematocrit.

7. The system of claim 5, wherein the switched capacitor accumulator can measure the phase measurement at high frequencies.

8. A method of measuring a property of a sample comprising:
   measuring an analyte in a sample;
   performing an analyte correction of the measured analyte due to one or more interferents, comprising:
      calculating an interferent impedance measurement including a magnitude measurement and a phase measurement using a switched capacitor accumulator to measure a phase angle; and
      adjusting the measurement of the analyte in the sample using the calculated interferent impedance measurement
   wherein measuring the phase angle comprises measuring time differences using the switch capacitor accumulator within a sample window of multiple setpoints of frequency in the range of 10 kHz to 500 kHz and accumulating the time differences that represent phase over a sample window to generate a signal large enough to be measured to calculate the phase measurement.

9. The method of claim 8, wherein the analyte is glucose and the at least one interferent is hematocrit.

10. The method of claim 8, further comprising applying a temperature correction to the interferent impedance measurement.

11. The method of claim 8, wherein the switched capacitor accumulator can measure the phase measurement at high frequencies.

* * * * *